（12）United States Patent
Florea et al.

(10) Patent No.: US 7,774,878 B1
(45) Date of Patent: Aug. 17, 2010

(54) RAPIDLY DEPLOYING EMERGENCY EVACUATION STRETCHER

(75) Inventors: Scott E. Florea, Dayton, OH (US);
Christine N. Florea, Dayton, OH (US);
Darnell G. Halsall, Miamisburg, OH (US); Carlos M. Powell, Beavercreek, OH (US)

(73) Assignee: Daytal LLC, Dayton, OH (US)

( * ) Notice: Subject to any disclaimer, the term of this patent is extended or adjusted under 35 U.S.C. 154(b) by 0 days.

(21) Appl. No.: 12/400,459

(22) Filed: Mar. 9, 2009

Related U.S. Application Data (60) Provisional application No. 61/106,707, filed on Oct. 20, 2008.

(51) Int. Cl.
*A47B 1/00* (2006.01)
(52) U.S. Cl. ............... 5/627; 5/625; 5/626; 5/628; 2/69.5; 2/102; 128/869; 128/870; 128/874; 128/876
(58) Field of Classification Search ............. 5/625–628, 5/494; 2/102, 94, 69.5, 69, 85, 93, 108, 247, 2/250; 294/140; 128/869, 870, 873, 874, 128/876
See application file for complete search history.

(56) References Cited

U.S. PATENT DOCUMENTS

| 6,216,296 | B1 * | 4/2001 | Carrasco | 5/625 |
| 6,477,728 | B1 * | 11/2002 | Faz | 5/625 |
| 6,634,044 | B1 * | 10/2003 | Wright | 5/625 |
| 7,607,184 | B1 * | 10/2009 | Goodner, Jr. | 5/627 |

OTHER PUBLICATIONS

Introduction of Modern Stretchers in Armed Forces for Improving Casualty Evacuation in Field with Special reference to Casualty Evacuation in Mountains, MAJAFI 2005; 61: 157-162.

* cited by examiner

*Primary Examiner*—Peter M Cuomo
*Assistant Examiner*—Nicholas Polito
(74) *Attorney, Agent, or Firm*—R. William Graham (57) ABSTRACT

A rapidly deploying emergency evacuation stretcher includes an article for easy transport on one's person, wherein the article is characterized to include a first mode of utility and a second mode of utility, and the article includes a lightweight flexible member which is packed in an undeployed mode and disposed adjacent the article in a manner which cooperates with the article in a manner to enable the first mode of utility substantially without interference thereof and unpacked in its deployed state and cooperates with the article in a manner to provide the second mode of utility which includes forming the stretcher. A method uses the rapidly deploying emergency evacuation stretcher to transport a person.

7 Claims, 13 Drawing Sheets

FIG.11

RAPIDLY DEPLOYING EMERGENCY EVACUATION STRETCHER

This specification claims the benefit of earlier filed U.S. Ser. No. 6,106,707 filed Oct. 20, 2008.

TECHNICAL FIELD OF THE INVENTION

The present invention relates to the field of transporting aids. More specifically, the present invention relates to an article for use in emergency situations for transporting an injured or ill person.

BACKGROUND OF THE INVENTION

There are situations where an individual becomes ill or injured in the field and it is necessary to move the person to a treatment site. This is often the case in the battle field, in rescue operations or in police/fire deployed environments. Other situations include hunters in a remote area who are injured. In any of these cases, it may be required that the fallen person be transported great distances on foot by others in the field so that aid can be administered. In some situations, such as battlefield, a delay or failure in providing transport may result in further injury or death.

Currently, moving such injured or ill party requires use of a stretcher which typically includes that a stretcher for transport must be produced at the site of the fallen person. The stretcher commonly includes a canvas material stretched between two poles and cross members. To carry this in the field while performing duties in the field is impractical as it is burdensome and adds extra weight to the bearer causing quicker fatigue than if not burdened with carrying a stretcher. Consequently, such persons in the field typically do not carry stretchers and when a person goes down the other persons do their best to drag out the injured party or carry them over one's shoulder. In some cases, the fallen party is left in the field until transport arrives. As a result, this significantly increases the risk of complication and death to a fallen party.

There is need to improve the method and means for removing a fallen party in the field with greater ease and without need for waiting for additional transportation equipment to arrive. The present invention overcomes the deficiencies of the prior devices.

SUMMARY OF THE INVENTION

Accordingly, it is an object to improve the method and means for removing a fallen party in the field with greater ease and without need for waiting for additional transportation equipment to arrive.

It is another object to provide a lightweight transportable stretcher.

It is still another object to provide a stretcher integrated into an article for transport on one's person.

It is yet another object to provide a stretcher integrated into an article of clothing.

Accordingly, the present invention is directed to a rapidly deploying emergency evacuation stretcher. The stretcher includes an article for transport on one's person in a field environment, wherein the article is characterized to include a first mode of utility and a second mode of utility. The article includes a lightweight flexible member which in its undeployed mode can be disposed adjacent the article in a manner which cooperates with the article in a manner to provide the first mode of utility and in its deployed state cooperates with the article in a manner to provide the second mode of utility which includes forming the stretcher. In a preferred embodiment, the article of clothing includes a vest, which can be a ballistic proof vest, and the light weight flexible member can include a flexible expanse material, such as mesh material. The article can include a compartment which houses the flexible expanse material.

Other objects will become readily apparent upon viewing the drawings and in reading the disclosure hereinafter.

BRIEF DESCRIPTION OF THE DRAWINGS

A more complete understanding of the present invention may be derived by referring to the detailed description and claims when considered in connection with the Figures, wherein like reference numbers refer to similar items throughout the Figures.

DETAILED DESCRIPTION OF THE PREFERRED EMBODIMENTS

Referring now to the drawings, the rapidly deploying emergency evacuation stretcher of the present invention is generally designated by the numeral 10. The rapidly deploying emergency evacuation 10 can include an article 12, such as clothing, which is intended to be worn by a person (not shown) in a field environment, such as a battle field, for example. Here the article 12 is shown in the embodiments to include a vest which can be of a ballistic proof type. However, it is contemplated by the instant invention that the article 12 can be integrated into other forms of clothing such as a coat, for example, of the type for use by firemen, law enforcement personnel or hunters although other more general uses are envisioned, such as hiker's or climber's clothing gear.

Figure 10A:
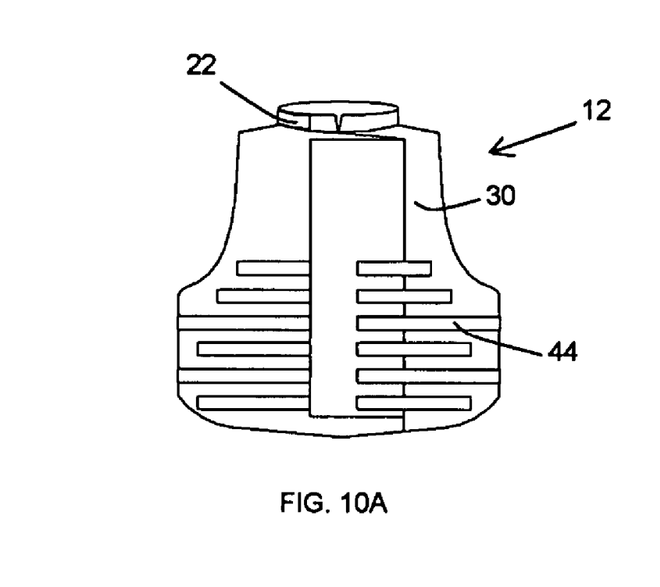
FIG. 10A depicts a front plan view of the embodiment in FIG. 6 in an undeployed mode.
Figure 10B:
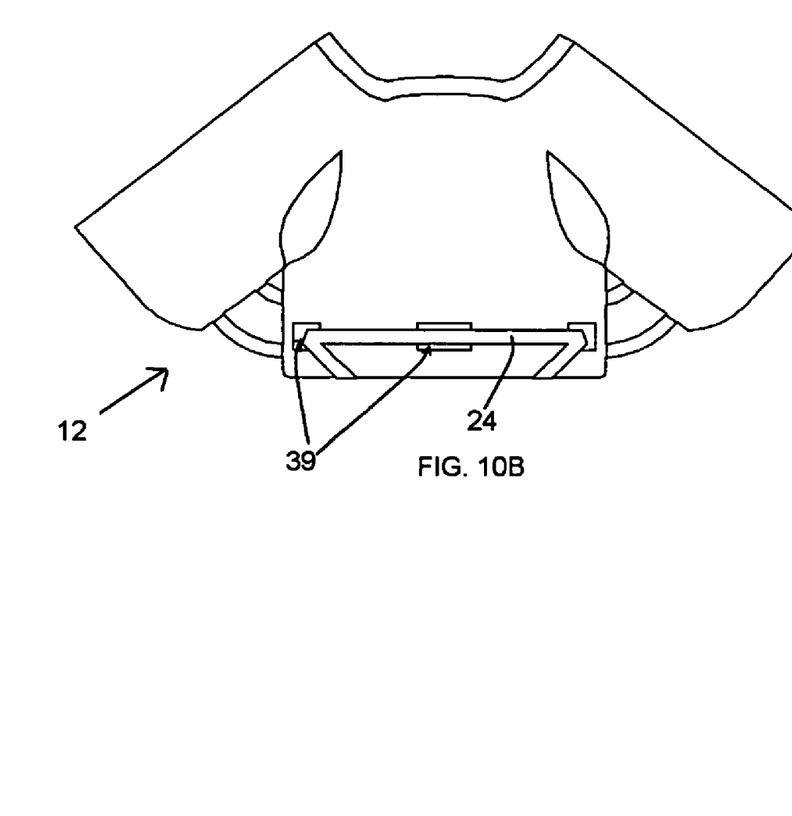
FIG. 10B depicts another view of the embodiment in FIG. 6 in an undeployed mode with an article in an open mode.
Figures 10C, 10D, 10E:
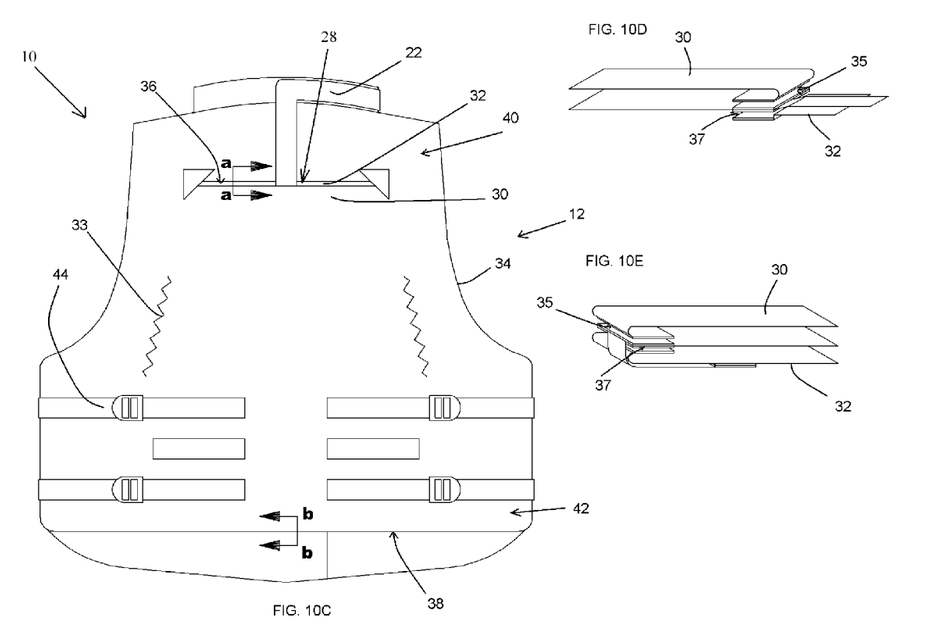
FIG. 10C depicts a back plan view of the embodiment in FIG. 6 in an undeployed mode.
FIG. 10D depicts an exploded isometric section through line a-a in FIG. 6C.
FIG. 10E depicts an exploded isometric section through line b-b in FIG. 6C.
Figure 11:
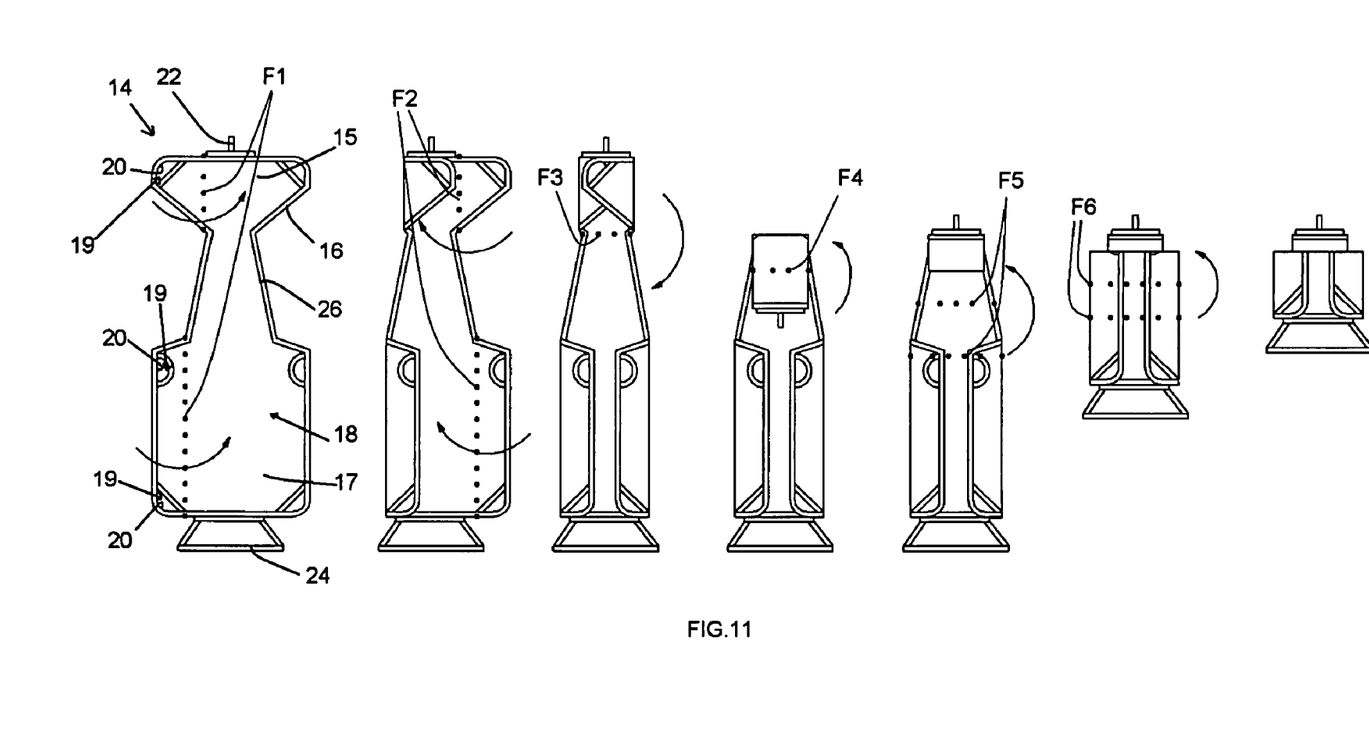
FIG. 11 depicts a folding sequence for a component of the invention.

It can be seen that the article 12 is characterized to include a first undeployed mode of utility as illustrated in FIGS. 5A-5C and 10A-10C, for example, and a second deployed mode of utility as illustrated in FIGS. 1-4 and 6-9. The article 12 can include a lightweight flexible member 14 which is best illustrated in FIG. 11 in which there is illustrated a method of folding the flexible member 14 for disposal adjacent the article 12 from its deployed mode to its undeployed mode. The flexible member 14 can be folded along fold lines F1-F6. The flexible member 14 can be disposed adjacent the article 12 in a manner which cooperates with the article 12 in a manner to enable article 12 to be used in its undeployed mode and in a conventional state without interference from the flexible member 14. This will be more fully understood in reading the following description.

The flexible member 14 can be of a high-strength, durable, light-weight material. Those skilled in the art will appreciate that other materials may be used. The flexible member 14 can include a peripheral strap 16 which can be made of a nylon, polypropylene, polyester or other high-strength, durable, light-weight material fabric to aid in carrying and further includes a flexible expanse material 18, such as mesh or cloth material, such as cotton, rayon, canvas, denim, or nylon. While not intended to be limiting, but for purposes of illustrating a desirable preferred embodiment, the flexible member 14 can be made in a general form of an hourglass (or rectangle) form fitting shape as seen in FIG. 11 for integrating with vest 12.

By virtue of the strap 16 having a sufficient strength, it lends itself well in forming handle portions 20 about the periphery of the flexible member 14 adjacent open regions 19 formed between strap 16 and expanse material 18. By way of example, there are shown six handles 20 spaced about the flexible member 14 with three handles 20 on each side.

Figure 1:
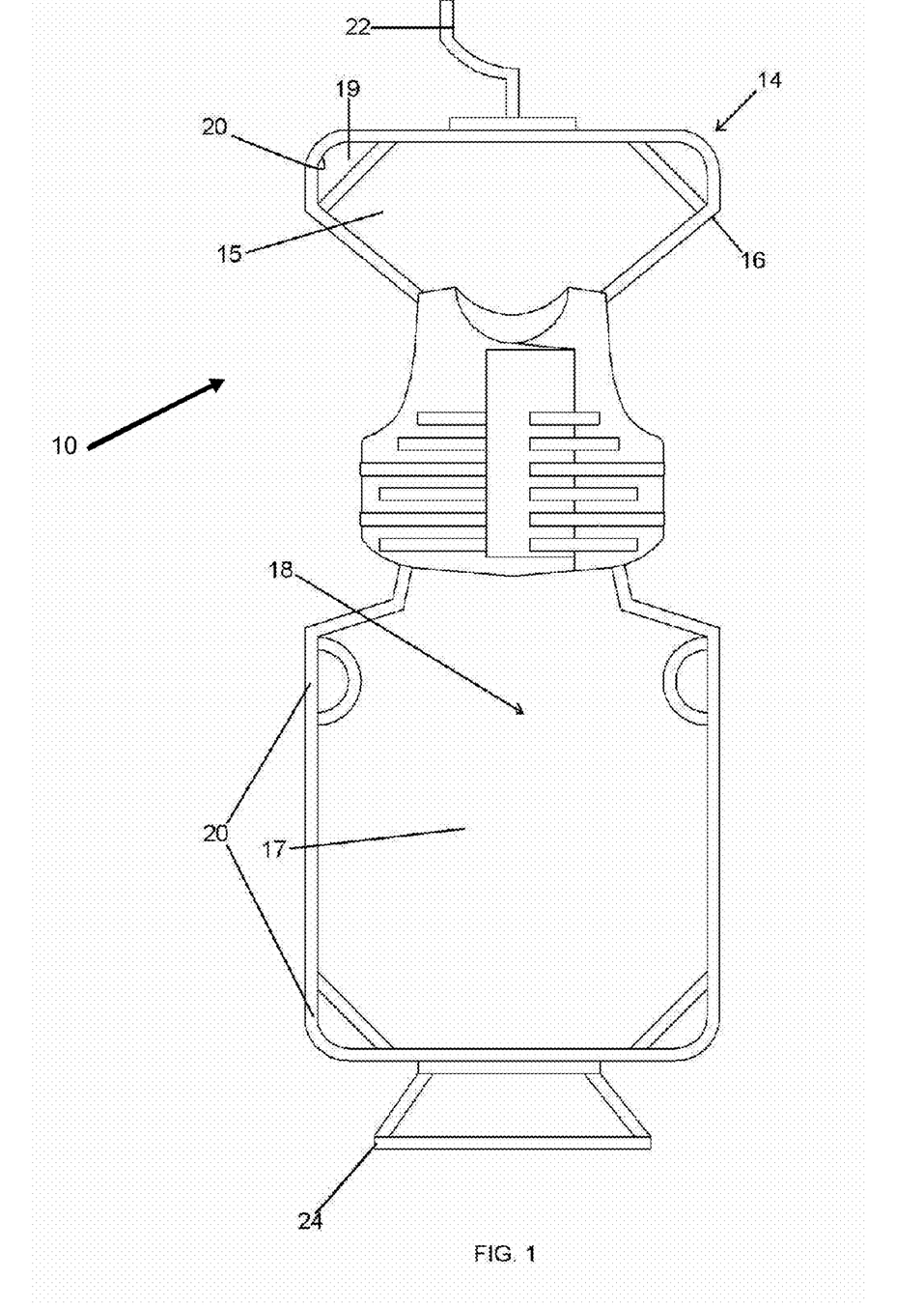
FIG. 1 depicts a front plan view of an embodiment of the invention in a deployed mode.
Figure 2:
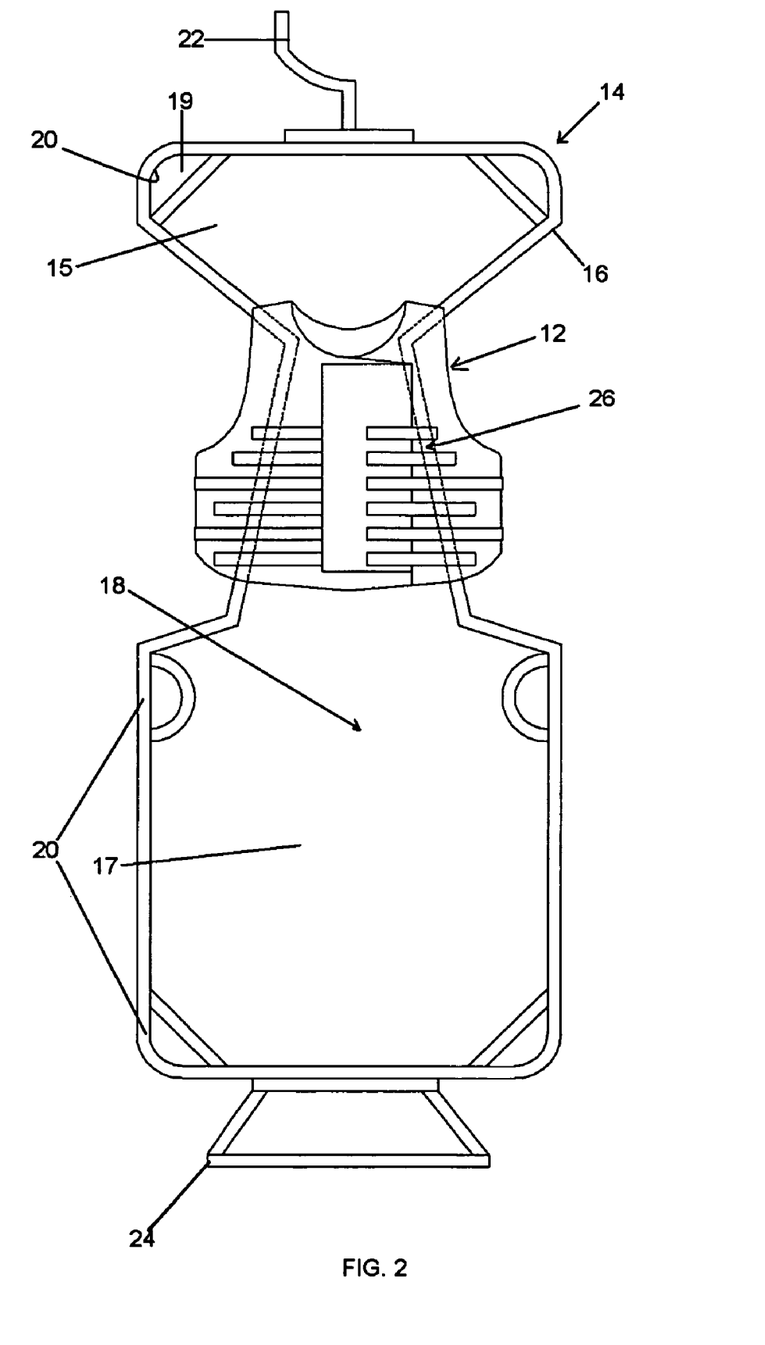
FIG. 2 depicts a front plan view of the embodiment in FIG. 1 revealing hidden lines of a flexible member in a deployed mode.
Figure 3:
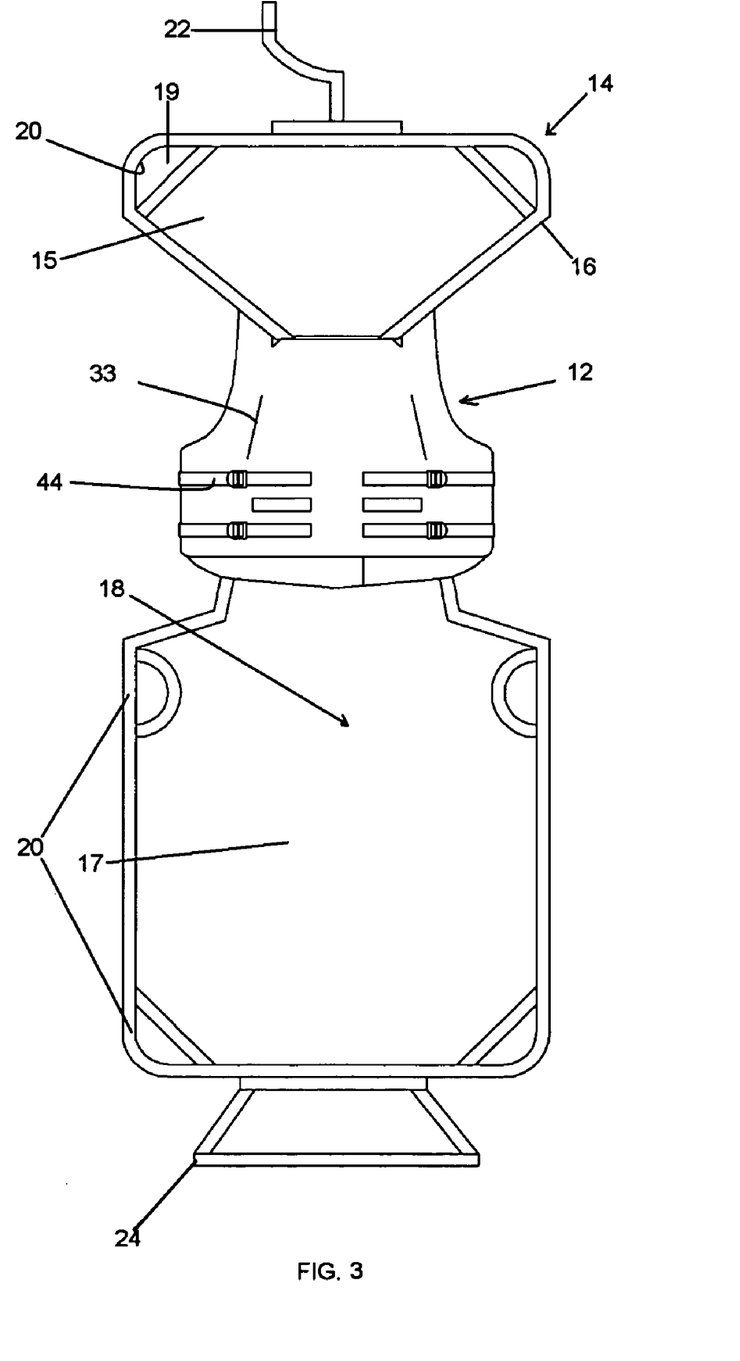
FIG. 3 depicts a back plan view of the embodiment in FIG. 1 in a deployed mode.
Figure 4:
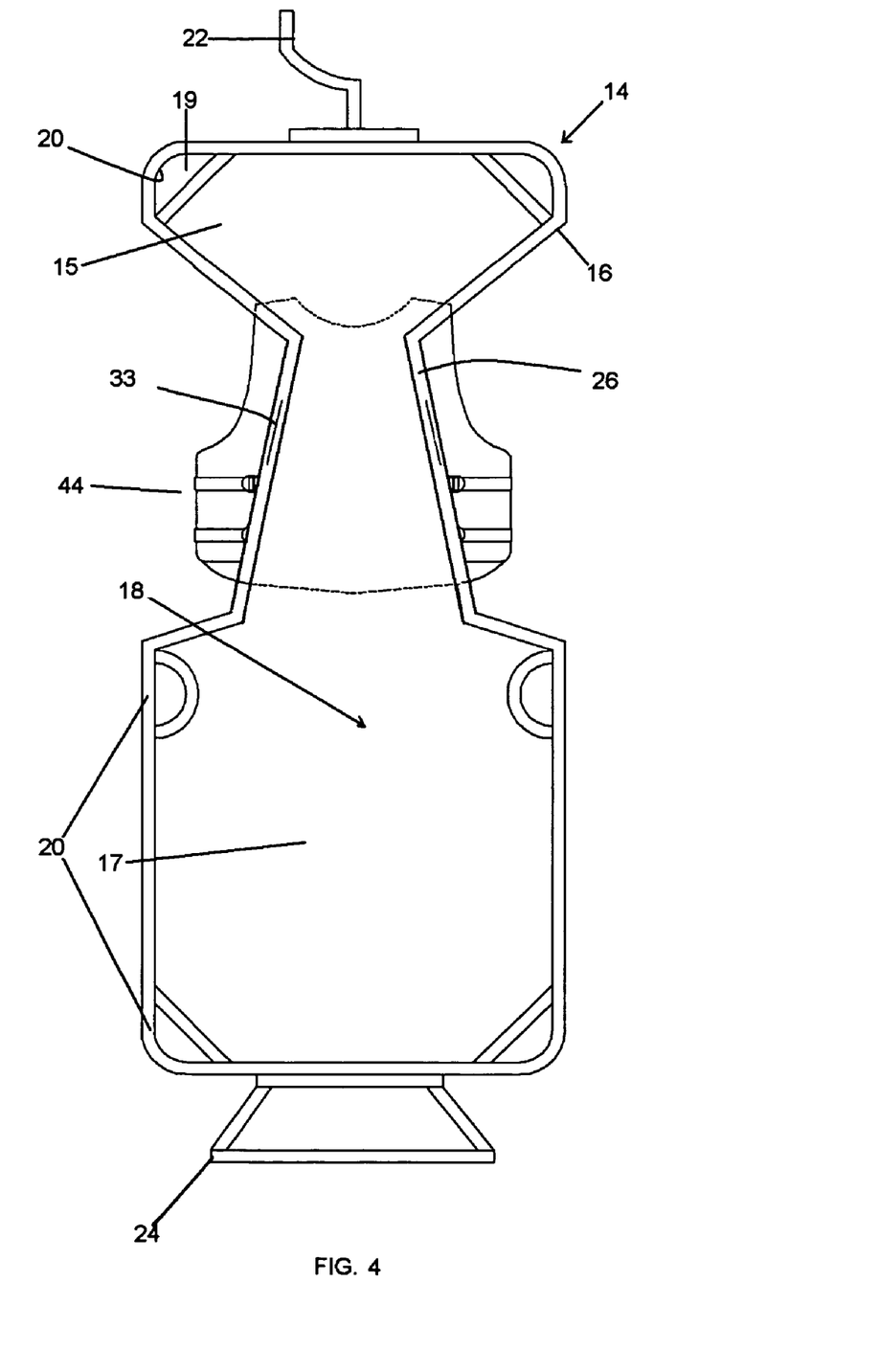
FIG. 4 depicts a back plan view of the embodiment in FIG. 1 in a deployed mode with part of a back of an article cut away to reveal the flexible member.
Figure 5A:
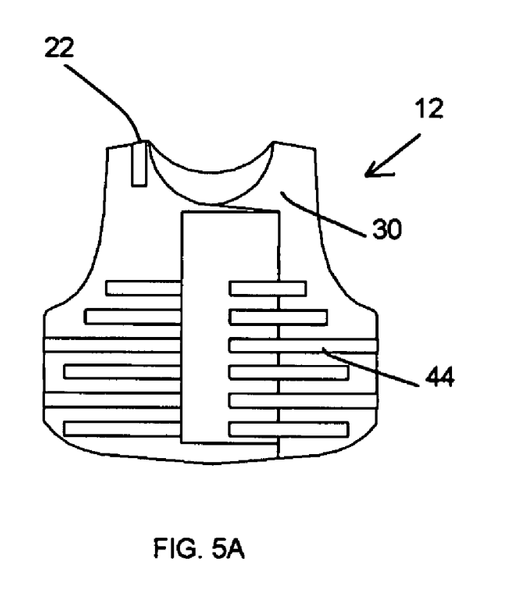
FIG. 5A depicts a front plan view of the embodiment in FIG. 1 in an undeployed mode.
Figure 5B:
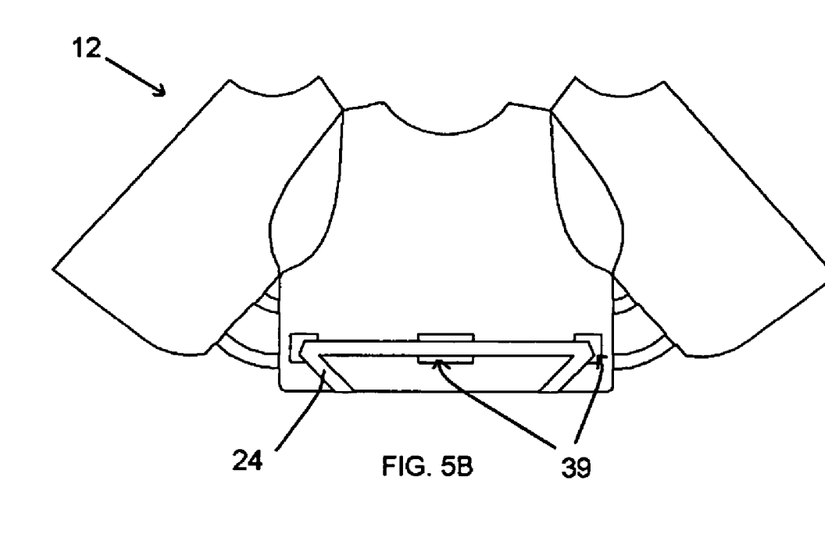
FIG. 5B depicts another view of the embodiment in FIG. 1 in an undeployed mode with the article in an open mode.
Figures 5C, 5D, 5E:
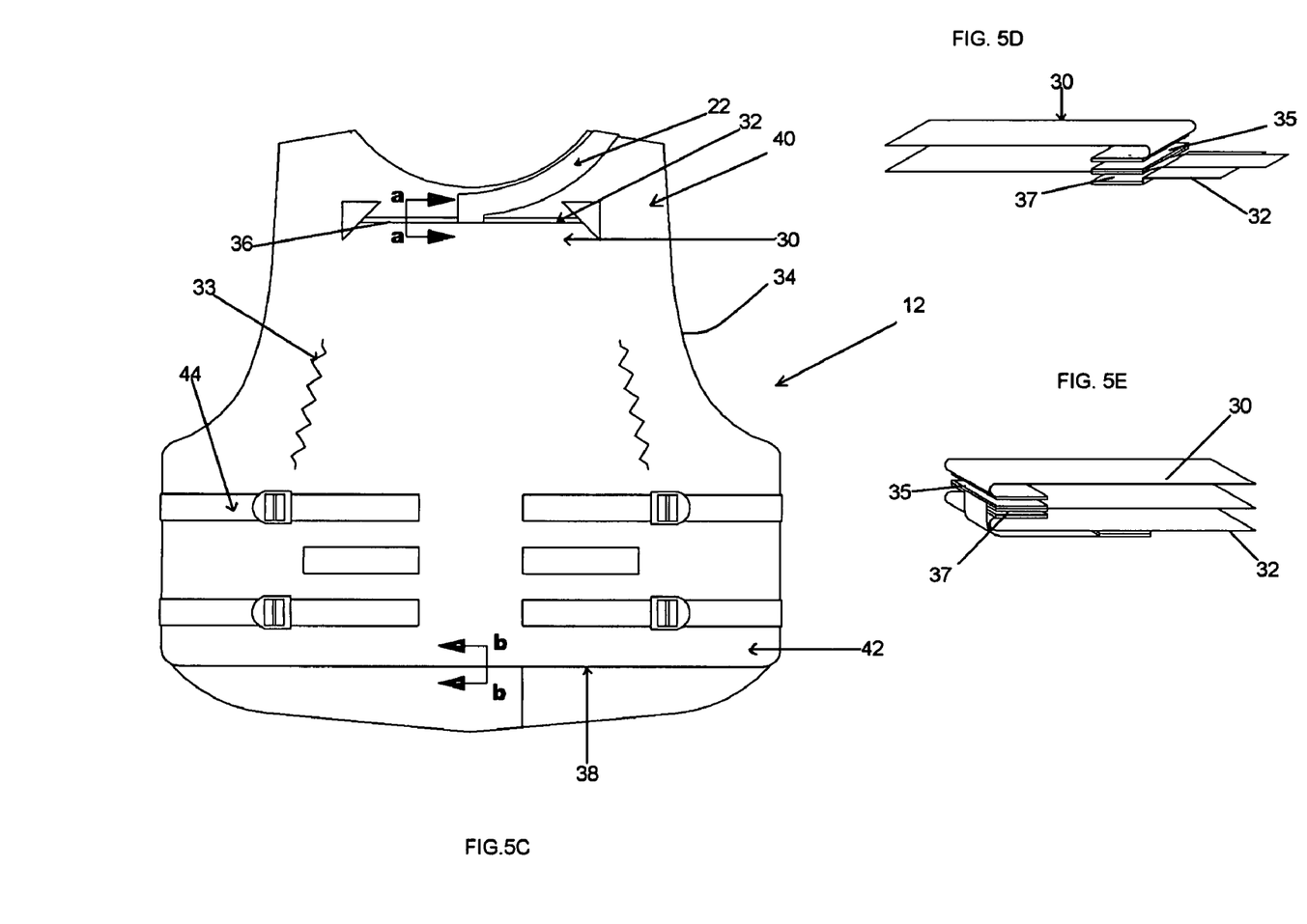
FIG. 5C depicts a back plan view of the embodiment in FIG. 1 in an undeployed mode.
FIG. 5D depicts an exploded isometric section through line a-a in FIG. 5C.
FIG. 5E depicts an exploded isometric section through line b-b in FIG. 5C.
Figure 6:
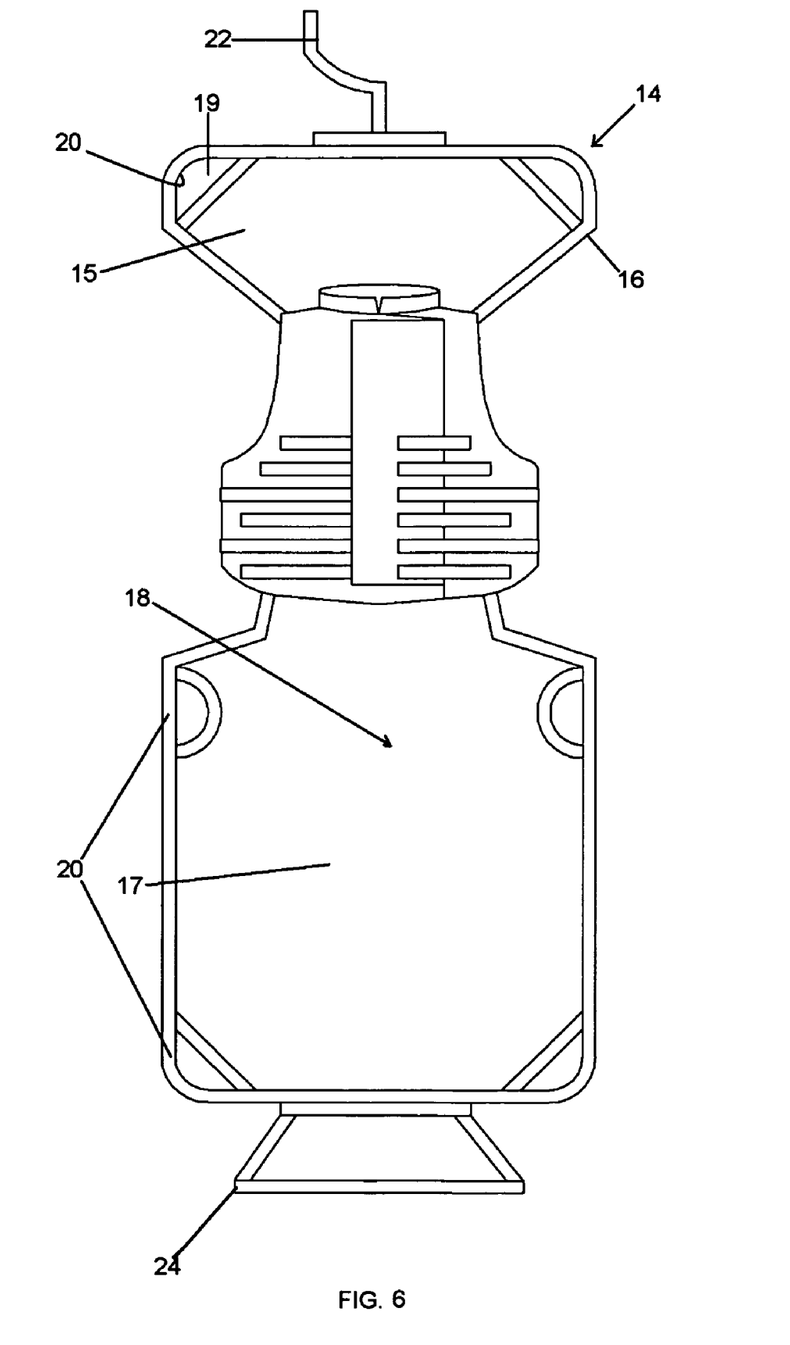
FIG. 6 depicts a front plan view of another embodiment of the invention in a deployed mode.
Figure 7:
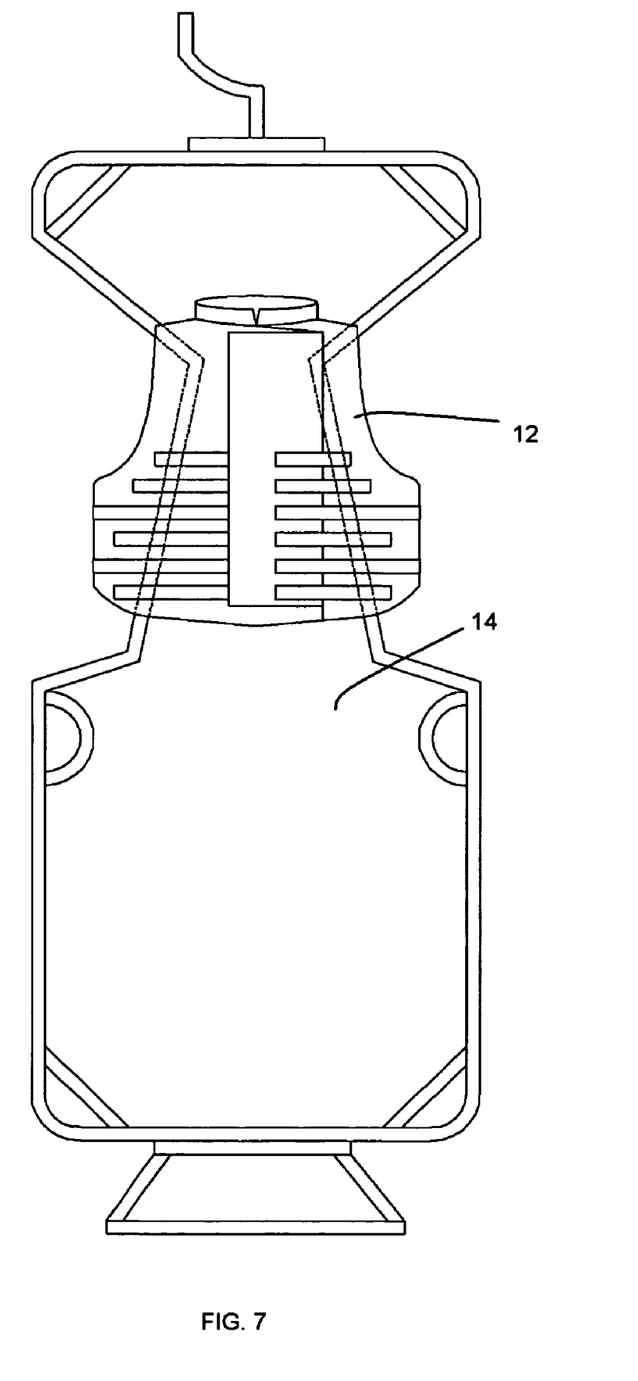
FIG. 7 depicts a front plan view of the embodiment in FIG. 6 revealing hidden lines of a flexible member in a deployed mode.
Figure 8:
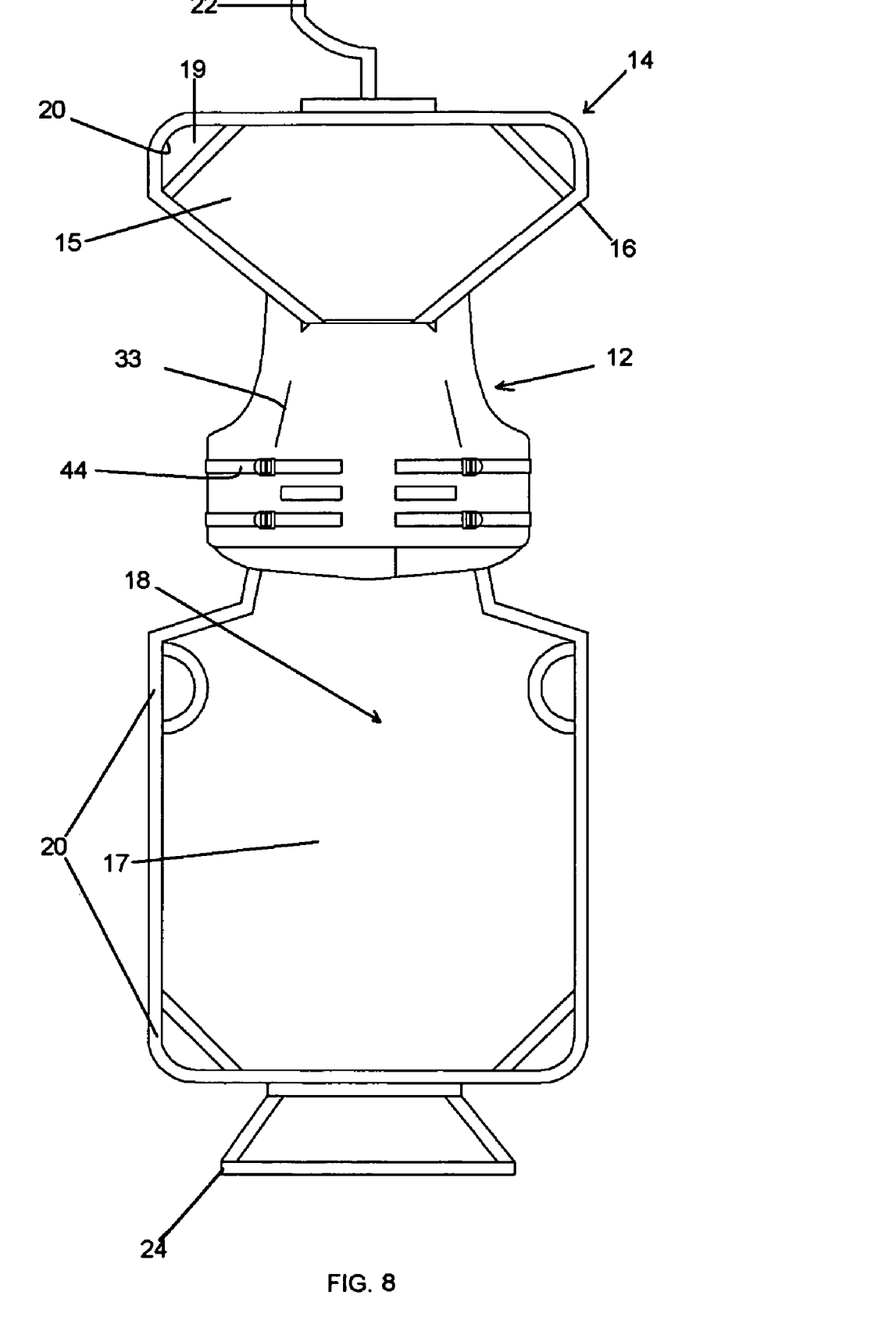
FIG. 8 depicts a back plan view of the embodiment in FIG. 6 in a deployed mode.
Figure 9:
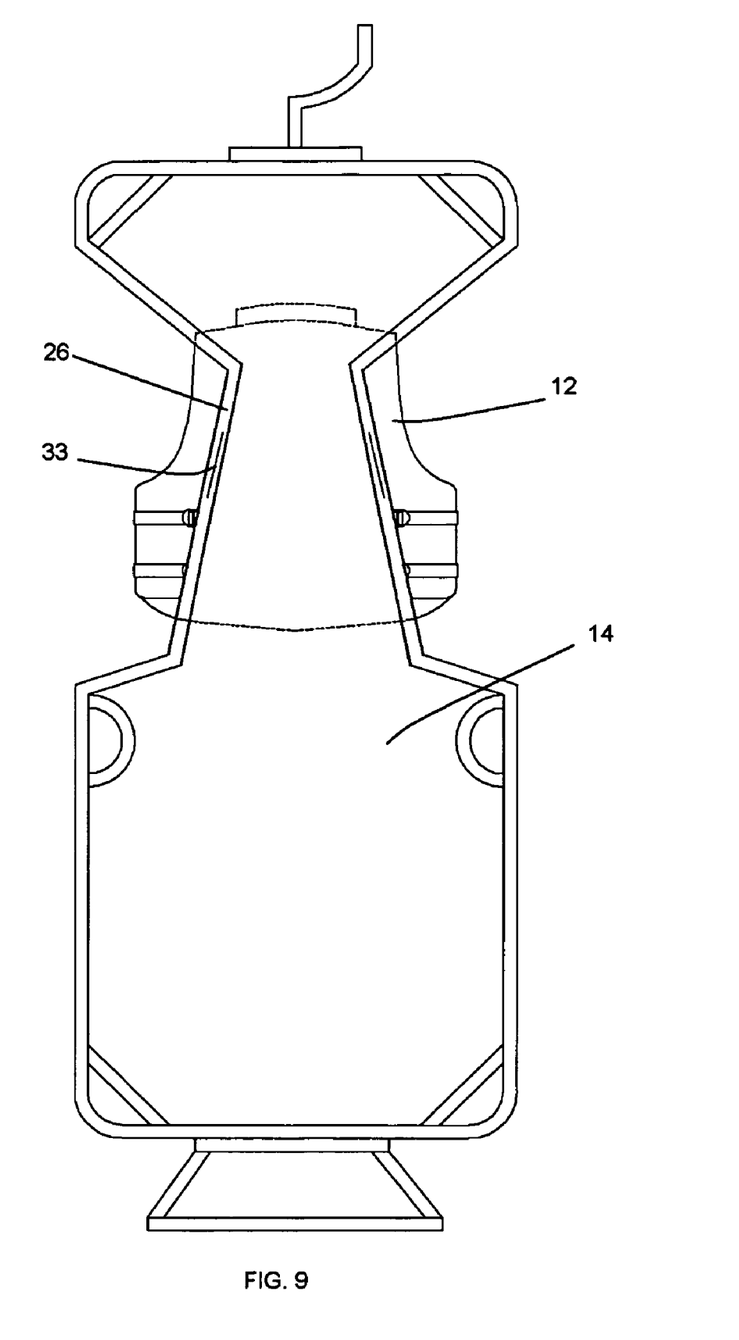
FIG. 9 depicts a back plan view of the embodiment in FIG. 6 in a deployed mode with part of a back of an article cut away to reveal the flexible member.

Additionally, the peripheral strap 16 can include end handles 22 and 24 to permit the deployment in a rapid fashion by pulling on end handles 22, 24. When packed flexible member 14 is packed in compartment 28, end handle 22 can be disposed outside of compartment around the neck and connected to outer layer 30 by means of hook and loop material (not shown) and handle 24 can be removably connected to vest 12 by means of hook and loop members 39 as seen in FIG. 5B. Portions 26 of strap 16 can preferably be stitched to the vest 12 inside a compartment 28. The compartment 28 can be formed between separate layers 30 and 32 of vest 12 which is depicted in FIG. 4, for example, wherein part of outer layer 30 is cut away from the figure to illustrate the compartment 28.

The compartment 28 can be formed by outer layer 30 and inner layer 32 which are connected at peripheral seam 34 and communicate with openings 36 and 38 at upper end 40 and lower end 42, respectively. The opening 36 can be formed in outer layer 30, for example, and layers 30 and 32 can include stitched hook and loop members 33 and 35 or other suitable fastening means to render the opening 36 closed. The opening 38 can be similarly formed in the lower end 42. In this way, the openings 36 and 38 can be closed to contain the packed flexible member 14.

In forming the rapidly deploying emergency evacuation stretcher 10, the portions 26 can be preferably stitched to one or both of the layers 30 and 32 in a secure manner, e.g., see stitches 33. It is conceived that other means of connection can be employed, such as snaps or hook and loop fasteners, for example.

In the preferred embodiments, the invention provides that the flexible member 14 be disposed adjacent to the article 12 so that a first mode of utility of the article 12, e.g., vest, be enabled. The vest 12 can typically be equipped with one or more outer utility straps 44 or holders which can be used to hold any number of items of the wearer's choice as preferred or mandated by trade or duty and with the flexible member 14 in undeployed mode, the utility of the vest 12 is enabled in an uninhibited manner. Additionally, the flexible member 14 in its deployed state cooperates with the vest 12 in a manner to provide the second mode of utility which includes forming the stretcher 10.

The rapidly deploying emergency evacuation stretcher 10 can be constructed in varying lengths and widths to accommodate persons of different sizes. The rapidly deploying emergency evacuation stretcher 10 can preferably have re-enforced stitched edges to increase load bearing ability as well as re-enforced stitching around all carry/drag handles 20 for extra security.

In preferred embodiments, the article 12 includes a vest, which can be a ballistic proof vest, and the light weight flexible member 14 can include a flexible expanse material, such as mesh material. The invention provides benefit to military, law enforcement personnel, firemen, first responders, hunters, hikers, backpackers, mountain climbers, skiers, explorers, and other outdoorsmen. The rapidly deploying emergency evacuation stretcher 10 can be used to safely transport a fallen party wearing the vest 12 by deploying using the flexible member 14.

The rapidly deploying emergency evacuation stretcher 10 can be deployed while on or off of the wearer as the case may be to aid fallen members in the field. Another feature of the invention is the configuration of the flexible member 14 and integration into the article 12. The flexible member 14 is configured to be compressed and folded reducing its size to fit into the compartment 28 which is relatively small area. The rapidly deploying emergency evacuation stretcher 10 can be extracted from compartment 28 to be deployed. It is envisioned that flexible member 14 in the case of it being removable from the compartment 28, can serve as rapidly deploying emergency evacuation stretcher 10 and be carried independently by a person in a suitable article having a compartment.

The rapidly deploying emergency evacuation stretcher 10 can be attached by fastening it directly onto the wearer. The flexible member 14 can be deployed from two separate openings 36 and 38 which are located at the shoulder area and the waist area respectively. The layers 30 and 32 and flexible member 14 can be held closed by a fastening system 35 and 37.

The hour glass form of the preferred embodiment allows for a more comfortable and stable fit for a wearer. When the wearer is injured the rapidly deploying emergency evacuation stretcher 10 can be deployed by separating the layers 30 and 32 from the flexible member 14 and depending on the number of people used for the extraction deploy only upper portion 15 of the flexible member 14, and optionally lower portion 17 by pulling on the corner handles, to remove the flexible member 14 from the compartment 28. Thus, depending on the number of persons aiding in the field, either one portion 15 or both portions 15 and 17 can be used for the extraction permitting the fallen party to be carried or dragged.

The rapidly deploying emergency evacuation stretcher 10 can be re-used after each use. The rapidly deploying emergency evacuation stretcher 10 can be made of a material which can be sanitized providing for a clean extraction system.

In the preferred embodiment, the layers 30 and 32 can be made of the same or different material. Those skilled in the art will appreciate that this is not a requirement of the present invention.

In the preferred embodiments, the article 12 is depicted in the form of a vest which as seen in the embodiments may take on different configurations. Those skilled in the art will appreciate that vest 12 may be openable, as depicted in FIGS. 5B and 10B. Alternatively, the vest may be formed of a single unopenable piece (not shown) as a pullover or combination thereof. There have been numerous previous proposals for ballistic vests and other protective armor that can be constructed to stop projectiles from most guns without injuring the wearer yet providing a construction that is light enough so that it can be conveniently worn. The invention can be easily incorporated in such vests and layers 30 and 32 and flexible member 14 may comprise sheets of ballistic nylon cloth or tightly woven aramid fiber, for example. Other forms of the article are envisioned and should not depart from the spirit of the present invention. Similarly, closure means 33 and 35 could alternatively include a zipper, snaps, buttons, etc., may be used without departing from the spirit of the present invention.

The rapidly deploying emergency evacuation stretcher 10 described provides a comfortable and easy way of carrying the same in field without unduly burdening the wearer. Further, the rapidly deploying emergency evacuation stretcher 10 fully enables other aspects of the article while in its undeployed mode to permit other desired or necessary activities of wearer. The rapidly deploying emergency evacuation stretcher 10 is well suited for use military, law enforcement personnel, firemen, hunters, hikers, backpackers, mountain climbers, skiers, explorers, and other outdoorsmen which potentially face risk of well being in the field. Although the preferred embodiments of the invention have been illustrated and described, it will be readily apparent to those skilled in the art that various modifications, derivations, and improvements may be made therein without departing from the spirit of the invention or from the scope of the appended claims.

What is claimed is:

1. A garment and integrated rapidly deploying emergency evacuation stretcher, which includes:
   a flexible garment for one's torso which includes a compartment having an upper opening and a lower opening, wherein said flexible garment is characterized to include a first mode of utility and a second mode of utility, and said flexible garment includes a lightweight flexible and non-rigid member having a first end and a second end and which is integrally connected to said flexible garment and packed in an undeployed mode and disposed adjacent said flexible garment in a manner which cooperates with said flexible garment in a manner to enable said first mode of utility substantially without interference thereof such that said garment and member remain non-rigid and unpacked in its deployed state such that said first end extends from said upper opening of said compartment and said second end extends from said lower opening of said compartment and cooperates with said flexible garment in a manner to provide said second mode of utility which includes forming a stretcher.

2. The garment and integrated rapidly deploying emergency evacuation stretcher of claim 1, wherein said flexible member includes flexible expanse material.

3. The garment and integrated rapidly deploying emergency evacuation stretcher of claim 1, wherein said compartment includes an upper portion to removably receive said first end and a lower portion to removably receive said second end.

4. The rapidly deploying emergency evacuation stretcher of claim 1, wherein said first mode of utility of said article includes one of a clothing equipped for military, police, firemen, first responders, hunters, hikers, backpackers, mountain climbers, skiers, explorers, and outdoorsmen.

5. The rapidly deploying emergency evacuation stretcher of claim 1, wherein said flexible member includes a handle.

6. The rapidly deploying emergency evacuation stretcher of claim 1, wherein said flexible member includes a plurality of handles.

7. The rapidly deploying emergency evacuation stretcher of claim 6, wherein said handles are formed on lateral portions of said flexible member.

\* \* \* \* \*